United States Patent
Simon

(10) Patent No.: US 11,207,010 B2
(45) Date of Patent: Dec. 28, 2021

(54) NEUROTHERAPEUTIC VIDEO GAME FOR IMPROVING SPATIOTEMPORAL COGNITION

(71) Applicant: The Regents of the University of California, Oakland, CA (US)

(72) Inventor: Anthony J. Simon, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/560,651

(22) Filed: Sep. 4, 2019

(65) Prior Publication Data

US 2020/0015726 A1 Jan. 16, 2020

Related U.S. Application Data

(62) Division of application No. 15/564,691, filed as application No. PCT/US2016/029321 on Apr. 26, 2016, now abandoned.

(Continued)

(51) Int. Cl.
*A61B 5/16* (2006.01)
*A63F 13/67* (2014.01)
(Continued)

(52) U.S. Cl.
CPC .............. *A61B 5/162* (2013.01); *A61B 5/168* (2013.01); *A61B 5/4836* (2013.01); *A63F 13/44* (2014.09);
(Continued)

(58) Field of Classification Search
CPC .......... A63F 13/44; A63F 13/67; A61B 5/162; A61B 5/4836
See application file for complete search history.

(56) References Cited

U.S. PATENT DOCUMENTS 6,422,945 B1 * 7/2002 Okita ..................... A63B 69/32
463/49
6,435,878 B1 8/2002 Reynolds et al.
(Continued)

FOREIGN PATENT DOCUMENTS

| WO | 2007070876 A2 | 6/2007 |
| WO | 2008027033 A1 | 3/2008 |
| WO | 201416483 A1 | 10/2014 |

OTHER PUBLICATIONS

Indu Vedamurthy et al., "A Dichoptic custom-made action video game as a treatment for adult amblyopia", Vision Research., vol. 114, Apr. 24, 2015, pp. 173-187.

(Continued)

*Primary Examiner* — Chase E Leichliter
(74) *Attorney, Agent, or Firm* — Park, Vaughan, Fleming & Dowler LLP

(57) ABSTRACT

The disclosed embodiments relate to a system that uses a video game to improve spatial and/or temporal information-processing capabilities of a user. During operation, the system enables the user to play the video game. During execution of the video game, the system first measures spatial and/or temporal information-processing capabilities of the user during the course of playing the video game. Next, the system uses the measured spatial and/or temporal information-processing capabilities to control a spatial placement and/or a temporal presentation rate of target items that the user is required to respond to during subsequent game play to stimulate enhancement of the user's spatial and/or temporal information-processing capabilities.

26 Claims, 9 Drawing Sheets

Related U.S. Application Data

(60) Provisional application No. 62/155,724, filed on May 1, 2015, provisional application No. 62/153,105, filed on Apr. 27, 2015.

(51) Int. Cl.
   *A63F 13/44* (2014.01)
   *A61B 5/00* (2006.01)

(52) U.S. Cl.
   CPC ............ *A63F 13/67* (2014.09); *A61B 5/7475* (2013.01); *A63F 2300/64* (2013.01)

(56) References Cited

U.S. PATENT DOCUMENTS

| | | | | |
|---|---|---|---|---|
| 8,251,818 | B1* | 8/2012 | Dunn | A63F 13/44 463/36 |
| 8,646,910 | B1* | 2/2014 | Schenkein | A61H 5/00 351/203 |
| 9,566,029 | B2* | 2/2017 | Faubert | A61B 5/16 |
| 2007/0066403 | A1* | 3/2007 | Conkwright | A63F 13/803 463/43 |
| 2007/0166675 | A1* | 7/2007 | Atkins | G09B 7/00 434/236 |
| 2007/0218440 | A1* | 9/2007 | Delahunt | G09B 7/02 434/236 |
| 2007/0293735 | A1* | 12/2007 | Chan | A61B 5/16 600/300 |
| 2008/0096660 | A1* | 4/2008 | Ota | A63F 13/10 463/39 |
| 2008/0161080 | A1* | 7/2008 | Terasaki | A63F 13/80 463/9 |
| 2008/0280276 | A1* | 11/2008 | Raber | A61B 5/16 434/236 |
| 2009/0069707 | A1 | 3/2009 | Sanford | |
| 2009/0104990 | A1* | 4/2009 | Tsujino | A63F 13/5255 463/32 |
| 2009/0111073 | A1* | 4/2009 | Stanley | F41G 3/2627 434/21 |
| 2011/0223999 | A1* | 9/2011 | Tsujino | A63F 13/10 463/37 |
| 2014/0011556 | A1* | 1/2014 | Kim | A63F 13/2145 463/7 |
| 2014/0100486 | A1* | 4/2014 | Alberts | A61B 5/1116 600/595 |
| 2014/0249447 | A1* | 9/2014 | Sereno | A61B 5/6898 600/558 |
| 2014/0349724 | A1* | 11/2014 | Seitz | G09B 23/28 463/9 |
| 2015/0031426 | A1* | 1/2015 | Alloway | A63F 13/44 463/9 |
| 2015/0126899 | A1* | 5/2015 | Ghajar | A61B 5/4064 600/558 |
| 2015/0170537 | A1* | 6/2015 | Super | G09B 7/00 434/236 |
| 2015/0305663 | A1* | 10/2015 | Roots | G09B 5/06 600/595 |
| 2016/0023099 | A1* | 1/2016 | Tymoszczuk | A63F 13/795 463/9 |
| 2016/0128893 | A1* | 5/2016 | Ooi | A61B 3/08 351/201 |
| 2016/0267804 | A1* | 9/2016 | Pemba | A63F 13/355 |
| 2016/0310059 | A1* | 10/2016 | Faubert | A61B 5/4088 |
| 2017/0300663 | A1* | 10/2017 | Paparella | A63F 13/67 |

OTHER PUBLICATIONS

Jessica D. Bayliss et al., "Lazy Eye Shooter: Making a Game Therapy for Visual Recovery in Adult Amblyopia Usable", In: "Medical image computing and computer-assisted intervention—MICCAI 2015: 18th International Conference, Munich, Germany, Oct. 5-9, 2015; proceedings", Jan. 1, 2013, Springer International Publishing, Cham 032548, vol. 8013, pp. 352-360.

Jessica D. Bayliss et al., "Lazy Eye Shooter: A Novel Game Therapy for Visual Recovery in Adult Amblyopia", 2012 IEEE International Games Innovation Conference, Sep. 1, 2012, pp. 1-4.

Omar Correa et al., "A New Approach for Self Adaptive Video Game for Rehabilitation. Experiences in the Amblyopia Treatment", 2014 IEEE 3rd International Conference on Serious Games and Applications for Health, May 1, 2014, pp. 1-5.

Extended European Search Report from EP Application No. 16786987.4 dated Sep. 7, 2018.

International Search Report PCT/US2016/029321, Searching Authority US, dated Jul. 26, 2016, Authorized Officer Blaine R. Copenheaver.

Green et al.; "Action-video-game experience alters the spatial resolution of vision", 88-94, 2007. [retrieved on Jun. 20, 2016] retrieved from the internet <URL:http://psych.wisc.edu/csgreen/csg_ps_07.pdf> entire document.

Spence et al; "Video Games and spatial cognition"; 92-104, 2010. [retrieved on Jun. 20, 2016] retrieved from the internet <URL:https://www.researchgate.net/profile/Ian_Spence2/publication/228091955_Video_Games_and_Spatial_Cognition/links/0912f50c2111fd11ec000000.pdf>, entire document.

Examination Report of the European Patent Office for EP Patent Application No. 16786987.4 dated Mar. 12, 2021.

* cited by examiner

NEUROTHERAPEUTIC VIDEO GAME FOR IMPROVING SPATIOTEMPORAL COGNITION

CROSS-REFERENCE TO RELATED APPLICATION

This application is a divisional application of, and hereby claims priority under 35 U.S.C. § 120 to, pending U.S. patent application Ser. No. 15/564,691, entitled "Neurotherapeutic Video Game for Improving Spatiotemporal Cognition," by inventor Anthony J. Simon, filed on 5 Oct. 2017. U.S. patent application Ser. No. 15/564,691 claims priority under 35 U.S.C. § 371 to PCT Application No. PCT/US2016/029321 entitled "Neurotherapeutic Video Game for Improving Spatiotemporal Cognition," by inventor Anthony J. Simon, filed on 26 Apr. 2016. PCT Application No. PCT/US2016/029321 claims priority under 35 U.S.C. § 119(e) to U.S. Provisional Application Ser. No. 62/155,724, filed on 1 May 2015, and to U.S. Provisional Application Ser. No. 62/153,105, filed on 27 Apr. 2015.

GOVERNMENT LICENSE RIGHTS

This invention was made with United States government support under Grant Nos. 1R01HD42974, 2R01HD42974 and 1R01HD46159 awarded by NIH/NICHD. The United States government has certain rights in the invention.

BACKGROUND

Field

The disclosed embodiments generally relate to therapeutic techniques for improving a person's spatiotemporal cognitive abilities. More specifically, the disclosed embodiments relate to the design of a neurotherapeutic video game that improves spatiotemporal information-processing capabilities of impaired individuals.

Related Art

There presently exist millions of people in the United States for whom the ability to mentally represent, and thus cognitively process, spatial and temporal information is impaired in some way, for example due to neurogenetic disorders, brain damage, or the effects of aging. When a person has a reduced ability to represent spatial and temporal information, the condition has significant functional implications. These reduced abilities also have follow-on implications, because the abilities comprise the foundation of a wide range of quantitative reasoning skills. For example, a person with such reduced abilities may have a hard time understanding numbers, distances, mathematics, time and money, and may not be able to travel by themselves. It may also be dangerous for these individuals to drive and they may be more likely to fall.

Hence, what is needed is a technique for improving spatial and/or temporal information-processing capabilities of a person with reduced abilities to process spatial and temporal information.

SUMMARY

The disclosed embodiments relate to a system that uses a video game that is specially designed to improve spatial and/or temporal information-processing capabilities of a user. During operation, the system enables the user to play the video game. During execution of the video game, the system measures a quality of mental representations of spatial and/or temporal information by the user during the course of playing the video game. (Note that this initial measurement can be used as screening tool for performance to be compared with group average to find those with impairments that are in need of intervention, e.g. 15/150 of kids in a grade school can be identified as having impairments.) The system uses the measured quality of mental representations of spatial and/or temporal information by the user to control a spatial placement and/or a temporal presentation rate of target items that the user is required to respond to during subsequent game play to stimulate enhancement of the user's spatial and/or temporal information-processing capabilities.

In some embodiments, controlling the spatial placement and/or the temporal presentation rate of the target items includes adaptively controlling the spatial placement and/or the temporal presentation rate based on ongoing measurements of the spatial and/or temporal information-processing capabilities of the user.

In some embodiments, measuring the quality of mental representations of spatial information by the user includes determining a spatial crowding threshold for the user based on how far apart in visual angle two target items can be while still being mentally represented as distinct unitary items by the user.

In some embodiments, measuring the quality of mental representations of temporal information by the user includes determining a temporal crowding threshold for the user based on how short a duration between appearances of two target items can be while still being mentally represented as distinct unitary items by the user.

In some embodiments, while adaptively controlling the spatial placement and/or the temporal presentation rate, the system presents the target items so that spatially distributed and temporally proximate target items are initially presented above the determined spatial and/or temporal crowding thresholds (i.e. within the existing capabilities) of the user. The system then adaptively presents the target items close to the spatial and/or temporal crowding thresholds of the user to stimulate enhancement of spatial and/or temporal functional abilities of the user. At all times, most of the items are presented within the central area in order to bias ongoing attention to the middle of the screen so that objects appearing in the outer rings maintain a greater, or more eccentric, visual angle than those in the middle. Presentation of items retains a normally distributed pattern around the center of the screen starting with almost all targets appearing centrally and then gradually beginning to populate more eccentric visual angles with increasing probability as player performance increases.

In some embodiments, while adaptively presenting the target items close to the spatial and/or temporal crowding thresholds of the user, the system adaptively controls an amount of stimulation provided to the user to an optimally adaptive level.

In some embodiments, adaptively presenting the target items close to the spatial and/or temporal crowding thresholds of the user involves: (1) increasing spatial distances measured in degrees of visual angle between target items when the user successfully responds to less than a threshold percentage of preceding target items; (2) decreasing spatial distances measured in degrees of visual angle between target items when the user successfully responds to a threshold percentage of preceding target items; (3) decreasing a duration between appearances of target items when the user successfully responds to a threshold percentage of preceding target items; and (4) increasing a duration between appearances of target items when the user successfully responds to less than a threshold percentage of preceding target items.

In some embodiments, prior to enabling the user to play the video game, the system performs a calibration step to calibrate a visual angle between target items that are presented on a display for the video game.

DETAILED DESCRIPTION

Figure 1:
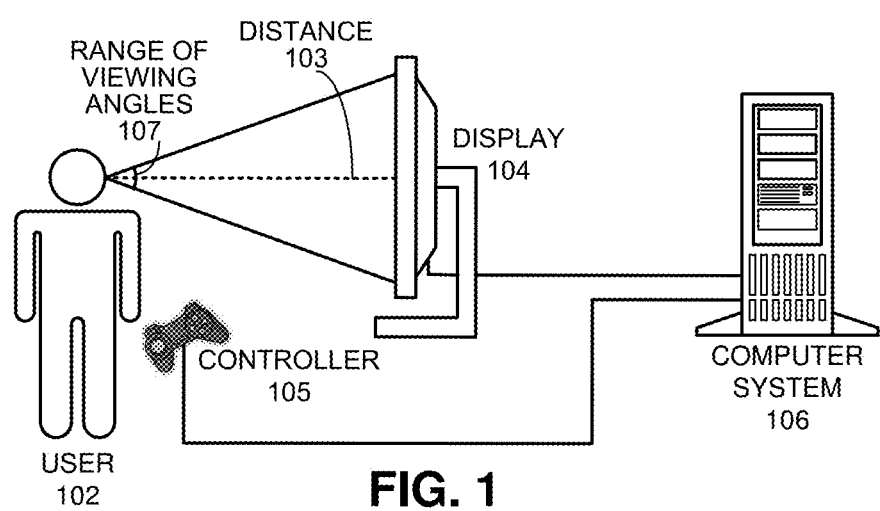
FIG. 1 illustrates a viewing angle for a user interacting with a video game in accordance with the disclosed embodiments.

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Overview of the Video Game

The disclosed embodiments adapt and improve upon the mechanics of existing action video games by using novel scientific data to change the games' operations so that the video games target the impaired spatial and temporal information-processing capabilities of players with one of several specified neurodevelopmental disorders. The effect is to deliver therapeutic stimulation with a resultant increase in spatiotemporal information-processing abilities. In doing so, these video games achieve results that cannot be achieved with existing "off the shelf" video games.

These new games are unlike existing games in several ways. Because they are designed to specifically alter cognitive function in a targeted group of players, they differ from entertainment games, which simply move the player toward increasingly complex play situations but do not intentionally seek to affect their performance. Because they are designed not just to improve performance but to change the actual neurocognitive underpinnings of specified mental activities, they differ from the majority of "brain fitness" or "brain enhancement" games, which generally adapt a well-tested experimental task from cognitive psychology and use it as a vehicle to generate better performance via mere practice effects. In any event, no existing video game has been developed to address the issue of decreased resolution and capacity of spatiotemporal information processing in individuals with neurodevelopmental disorders, individuals who have suffered brain injuries, healthy aging individuals, or those who have no diagnosis but still have impairments in these domains of cognitive function.

Figure 9:
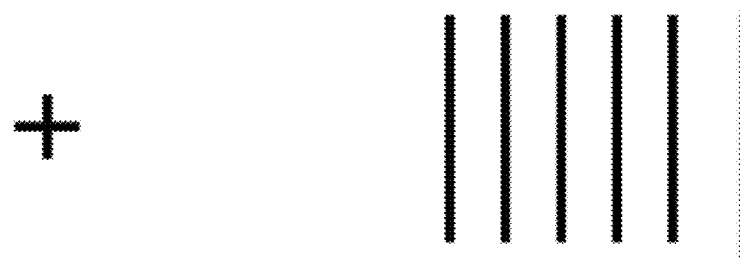
FIG. 9 illustrates an example image that illustrated the concept of crowding in accordance with the disclosed embodiments.

The games described in this specification have a specific and novel goal, which is to fundamentally change the spatial and temporal resolution, or degree of detail in which items in the real world can be accurately mentally represented as unique entities in the brain of the user. Together, these changes result in an increased capability to comprehend, understand and develop higher level cognitive abilities that depend upon spatiotemporal competence. One advantageous feature is that the complexity or difficulty of the game presented to the players in the entry stages of game play is controlled in such a way that it only presents the targets to which players are required to respond above the player's spatial and temporal information-processing threshold, in other words, at levels that present no difficulty for the current ability of the player. When multiple objects or events are presented in space and/or time that are too close for the viewer to mentally represent each of those objects or events as uniquely separable representational units, the phenomenon of "crowding" is said to have occurred. The point at which that occurs will be referred to as the crowding threshold. A spatial crowding threshold can be conceptualized as a specific measurement of the smallest distance in space (measurable in degrees or fractions of degrees of visual angle) between at least two targets on the screen, viewed at a specified distance in order to hold constant visual angle, at which each of the items can be individuated. This means that each item can be perceptually identified and resolved and then given a unique identifying token in the viewer's mental representation. These unique tokens can then be taken as inputs for other cognitive processes, such as counting. Practically, this means it is a specification of the limit, in spatial terms, of how far spread apart the two or more objects can be while still being recognized by the viewer as being viewable at the same time. At spatial distances smaller than specified by that threshold, the phenomenon of spatial crowding occurs due to some degree of overlap in the player's mental representation of one or more of the target objects. When parts of an individual representational unit overlap with those of another, they lose their unique identifying properties and the mental units representing each physical object on the screen cannot be reliably processed independently of one another. In other words, they are no longer mentally represented as unique entities even though there is a clear and measurable distance between their physical referents, i.e. the objects on the screen that they represent. One clear example of this situation is illustrated in FIG. 9 where 5 identical and identically spaced vertical black bars on a white background induce crowding and only 3 or 4 unique mental representations can be maintained and processed, leading to undercounting of the actual physical items. At spatial distances larger than specified by that threshold (i.e., at a greater spatial distance between the targets) all objects that appear can be perceived, resolved and uniquely mentally represented the player's cognitive machinery and subsequently taken as inputs by other processes, such as counting. If the counting process is executed correctly over the unique representational tokens, an accurate count of the physical items on the screen will result. At temporal "distances" smaller than specified by that threshold, the phenomenon of temporal crowding occurs due to some degree of overlap in the player's mental representation of one or more of the targets. Consequently, a player will not be able to uniquely represent and then process information about the object or event appearing at timepoint A and still create another unique representational object for another object or event subsequently appearing at the later time-point B (and, where applicable, C, D . . . ). In such cases, a mental representation of the second item cannot be created by the viewer and so cannot be examined or processed. It is thus not mentally represented as having existed, although it can be known that its physical referent did exist. At temporal "distances" greater than specified by that threshold, the phenomenon of temporal crowding does not occur and there is no overlap in the player's mental representation of one or more of the target objects or events. Consequently, a player will be able to uniquely represent and then process information about the object or event appearing at time point A and still create another unique representational object for another object or event subsequently appearing at the later time point B (and, where applicable, C, D . . . ). In such cases, the second item will be mentally represented by the viewer and can be reported and be taken as inputs other cognitive processes. To achieve reductions in spatial and temporal crowding requires at least two items to be designated as targets. For spatial crowding reduction the targets will be presented simultaneously, for temporal crowding the targets will be presented sequentially, with one being defined here as the Target 1 (also known as a "temporal cue") and subsequent ones being defined here as Targets 1+n (starting with n=1 or Target 2, also known as the "temporal target" in a cue-target pair as required by the attentional blink phenomenon (see for e.g. Sheppard, D. M., Duncan, J., Shapiro, K. L. & Hillstrom, A. P. Objects and events in the attentional blink. *Psychol Sci* 13, 410-415 (2002)).

Adaptive threshold-setting techniques are explained in more detail below, but to preview here, initial thresholding is determined in one of two modes. One is a person-specific mode (individual mode), where an individual takes part in a research study and has his or her spatial and temporal information-processing thresholds measured by the cognitive processing and psychophysical measures in the study. Then, these measured values are used to explicitly set the level of difficulty for the games to be played by that person. The other mode is a population-specific mode (population mode), wherein, for example, estimates are made of a group of children's thresholds based on the average of a large sample of children taking part in a research study (e.g., seven-year-old girls with full mutation fragile X syndrome), and those children subsequently play the games starting at a different level of difficulty than children from another group (e.g., typically developing seven-year-old girls). Another advantageous feature is that the adaptive manner in which the game regulates difficulty and reward is determined by the player's ability to respond to those items (i.e., targets) whose spatiotemporal characteristics the game manipulates.

During operation of the video game, the spatiotemporal complexity is constantly adjusted, based on the player's ongoing performance, in order to keep each player optimally stimulated by constantly presenting his or her neurocognitive capabilities with spatiotemporal information that is targeted just above and below the player's current crowding thresholds. Based on existing research findings, this is expected to alter these individuals' neurocognitive processing capacities due to increased resolution, and thus reduced crowding, of mental representations for spatial and temporal information in a significant and long-lasting manner. This enables them to meaningfully process, comprehend and learn about new information that was previously incomprehensible to them. (Note that the initial stages of thresholding can be use in a screening mode, e.g. to screen all $3^{rd}$ graders in a school district to identify unknown cases of impairment due to initial performance lower than peers and then use rest of intervention to reduce the impairments.)

The above-described technique is novel because it takes an established form of an engaging and cognitively demanding activity, namely computer-based action video game play, and adapts it to operate in a way that is unlike existing games. The technique creates a video game that enhances impaired cognitive functions in children with certain neurodevelopmental disorders (in particular, chromosome 22q11.2 deletion, aka Velocardiofacial/DiGeorge syndrome, fragile X syndrome, Turner syndrome, or Williams syndrome). Unlike commonly available video games, the above-described video games achieve this effect by targeting specific information-processing systems in a way that changes the nature of the information that they represent and process. This stands in contrast to other video games, even those with a therapeutic goal, that tend to achieve altered performance in terms of speed and accuracy changes that are the result of mere practice.

The technique is non-obvious because it requires the combination of two previously unconnected bodies of scientific literature, both of which are relatively new. The first of these identifies specific impairments in spatial and temporal information processing as the critical foundation of learning difficulties and developmental delay in children with one of several neurodevelopmental disorders, some of which have been described above. These impairments are hypothesized to arise from reductions in the resolution of mental representations for spatial and temporal information in the minds and brains of affected individuals. This compromises their functioning in these domains, and also in those areas of higher cognitive function that depend on these lower level functions. An analogy can be made to digital image resolution by pointing out the disadvantages of processing spatial information represented in an image captured by a one megapixel digital camera compared to the same computations carried out on an image captured by a 10 megapixel camera. These cognitive impairments can be linked to specific anomalies in developing brain structure that are consistently implicated in the role of spatial and temporal information neural circuitry.

Therefore, in order to create a novel therapeutic technique for enhancing spatial and temporal information processing in children (and adults) with specific cognitive impairments and thereby reduce, or even eliminate disability, we use the general principles of action video games in clearly specified ways. These video games are unlike any that currently exist because they use the immersive and motivating environment of the action video game to generate in the player mental activity specifically targeted at enhancing spatiotemporal cognitive functioning. What makes this type of video game different from existing technologies is that, akin to a drug development process, it proposes to construct a specific "compound" (the precise characteristics of the video game's cognitive requirements) targeted to specified cognitive functions and mental representations, which constitute the necessary "receptors" (the precise neurocognitive systems in which impairments create the learning difficulties) through a clearly defined delivery vehicle through the mechanics and interactive experience of action video game play. Currently, there are no other video games developed with this goal, that use game play in this manner, that deploy this specific science base to arrive at a final product, or that are aimed at remediating this specific area of neurocognitive function.

An enabling component to the technique is the technology of video gaming, specifically the action video game modality. This category of action video games comprises a vast array of different kinds of games including the sub-genres of platform games (where the player controls a character that jumps from one static or moving platform to another); first-person (or sometimes third-person) shooter games, where the player views the action from the point of view (POV) of a character shooting at moving objects or other characters; and fighting games, where the player takes the role of a character involved in some kind of direct combat with other characters. Despite the enormous variability in action video games, a common feature is that their greatest emphasis is not placed on tactical or strategic thinking. Rather, the central characteristic of interest here is that they all organize the critical aspects of game play around speeded processing of dynamic information and stress the integration of information across space and time as one of the main criteria for determining performance of the player. The fact that targets are usually spread across a wide visual field also creates a further challenge to resolution of mental representation since this degrades with increasing eccentricity from central viewing. For the purposes of simplicity, the term Action First Person Point of View (aFP-POV) game is used in this specification, although variants using $3^{rd}$ Person Point of View embodiments will likely be just as appropriate. Using an aFP-POV game design, which deploys the kind of interaction with the presented material just described, our system achieves cognitive enhancement through controlled and targeted stimulation of spatiotemporal representation systems. Such an outcome cannot be achieved with other kinds of video game genres, which include life simulation games, strategy games, role playing games, puzzle or computerized versions of board games or even the newly named genre of "exergames," such as games associated with the Wii Fit™ or related products. The aFP-POV design is advantageous because of the way that it stimulates the neurocognitive systems required to create the specified outcome in the player.

One embodiment of the aFP-POV game comprises a "shooter-style" game in a three-dimensional game playing mode. If other styles of play, such as flight or other vehicle simulator games, are created to fit the stated requirements, then they can be substituted. Many tools for developing aFP-POV shooter games exist and any could be used, but one embodiment is based on the existing "Unity" game development engine, which is a cross-platform game engine developed by Unity Technologies of San Francisco, Calif. An engine of this sort provides templates for objects to be involved in the game, along with the necessary physics to make them perform in a fashion consistent with the physical environment. It also provides templates for characters or avatars to whom the "camera" can be attached in order to provide the player's first person point of view in the game. It is not necessary that any specific existing engine be used, only that the resulting game is consistent with the performance aspects provided by such engines. The advantageous aspects of the aFP-POV shooter game to be developed are twofold. These aspects relate to: (1) the way that the game presents information to the player; and (2) the way that the game responds to the player's behaviors. The interaction between these two aspects is referred to henceforth as the aFP-POV's game "dependencies," and is described below in more detail.

Figure 5:
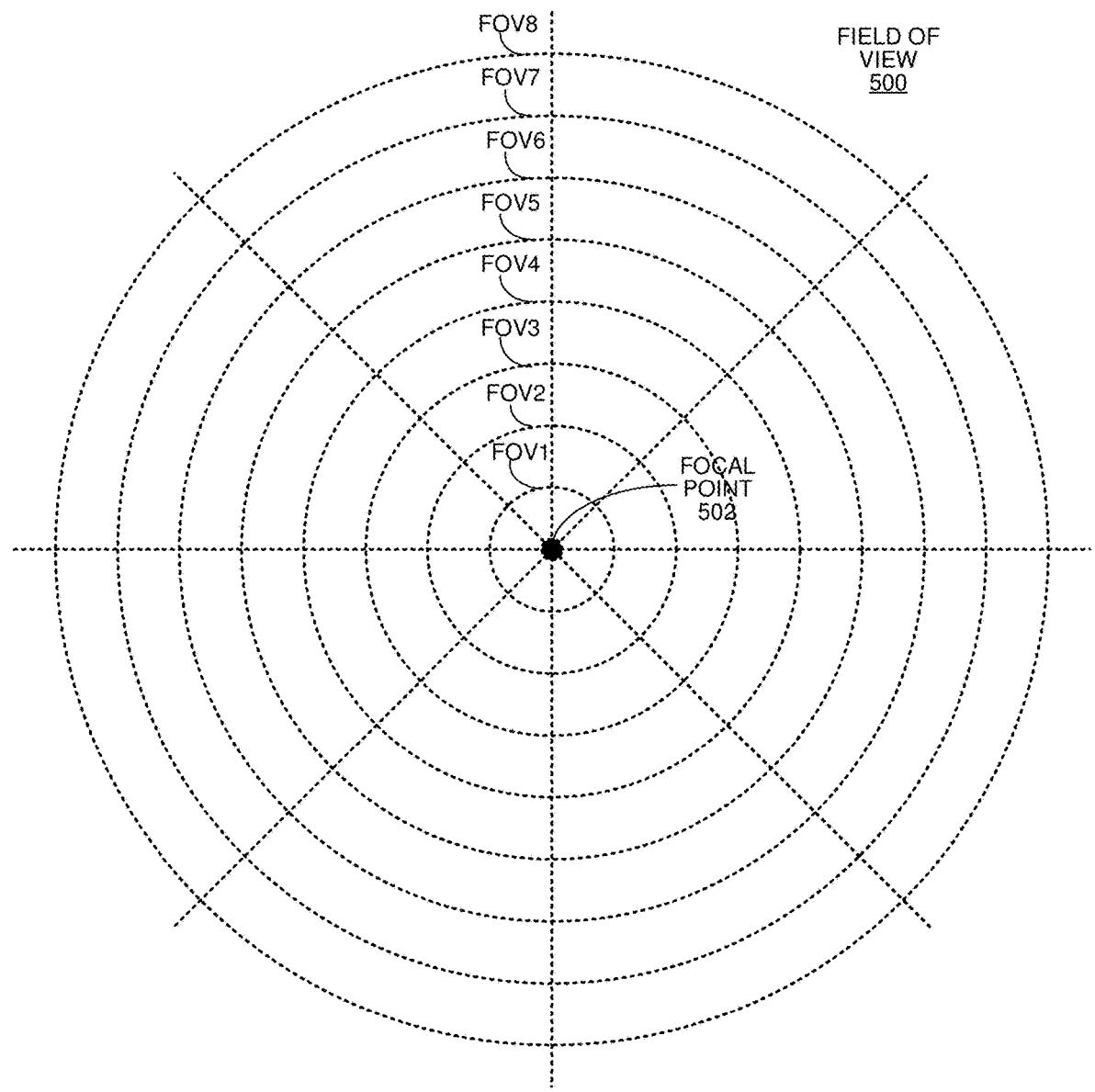
FIG. 5 presents an exemplary field of view for a video game in accordance with the disclosed embodiments.

The portion of the screen in which game play actually takes place is called the Field of View (FOV) (see FIG. 5). An advantageous feature of the game design is that the FOV is defined as a set of concentric circles (not visible to the player of the game). Each circle subtends about two degrees of visual angle when viewed from 60 cm from the screen (about arm's length). Each of these can be further subdivided into much smaller concentric circles to allow the algorithm the change the spatial distances between more than one target above or below the spatial crowding threshold in order to challenge that aspect of resolution. Similarly, it allows for finely specified placement of sequential targets above or below the temporal crowding threshold in order to challenge that aspect of resolution. In between any two circles in the display (i.e., an area covering 2 degrees of visual angle) there can be up to 118 smaller concentric rings measured in arcmin, which is a unit of $\frac{1}{60}^{th}$ of a degree of visual angle, for a total of 120 possible concentric circles including the original two FOV concentric circles. The design point of using a maximum spacing of two degrees of visual angle between each main circle was selected because eye movements cannot be made within this range, so this size of circle ensures that all the information encapsulated within it is available for visual processing by the player. Thus, only about a tenth of the standard video game play "arena" is covered by each of these circles, so that it takes at least 10 of them to cover the entire viewing area usually used in current video games. An alternative version of the game uses different sizes for each circle. Another advantageous feature of the design, that is not currently embodied in any known existing game, is that target items, which the player is required to respond to in order to influence the behavior of the game, are initially presented in a spatial location within the FOV, and at a presentation rate or Rate of Viewing (ROV) that is below, but close to, the spatial and temporal crowding thresholds of a targeted player of the game. Note that the initial spatial location of a target or targets can be within the central concentric circle (FOV1) because its two-degree extent ensures that visual information is processed by the foveal region of the retina, where the highest resolution of visual information processing is possible. The initial time lag between viewing of target items (ROV1) can be about two seconds. Changes to the ROV are determined by testing, but the rate (i.e., decrement in time between presentation of one target and the next) is not decreased below 100 milliseconds between targets. The parameters for this embodiment have been chosen based on currently available scientific data. Despite the fact that no known data exists for children with the disorders to be targeted here, studies of the "attentional blink" (a phenomenon that describes how close in time two temporally-spaced targets appearing in the same spatial location must be presented before the second one is unattended) show that the threshold is around 500 milliseconds for typical adults, and around 1.5 seconds for children with learning difficulties. Presenting information at or near the appropriate thresholds ensures that the player is able to respond with a degree of success parameterized to be about 80% in order to make the game entertaining and to provide immediate feedback of success and mastery, thereby making it both enjoyable and motivating. Therefore, two seconds is a reasonable initial ROV. If the initial ROV were significantly faster (i.e., a shorter temporal duration between targets was used), then presented information may not be represented and processed by young children, and the intervention would not have the desired effect because no stimulation of the temporal information system would be provided. Similarly, if the time between successive target items is much longer than 2 seconds, then changes would either be too large in magnitude to be imperceptible to the player, or more changes to the rate would have to be made than is desirable before any therapeutic effect could be gained, and the positive impact on temporal processing would lag behind that being provided for spatial information processing.

The above-listed parameters can be set by using research-validated measurement tools for the specific populations to which the game is targeted. In one embodiment of the system, the initial parameters can be set in one of two ways. In a "population mode," the parameters are chosen from a menu of populations already tested, and the resulting values are the average of those generated for children of the specified population for the age provided. In an "individual mode," the parameters are generated for the specific child (or adult) as a result of that child's (or adult's) participation in a research study once that has taken place. Neither of these options is present in any existing games. Once game play begins, the parameters used to determine the spatial and temporal characteristics of target stimuli are determined by the mechanics of the game, as described below.

One difference between our game and existing games is the way in which changes in the demands of the game are made in response to the performance of the player. No games currently exist in which spatial and temporal information processing is measured dynamically during the course of game play and then fed back into the game to directly affect the specifics of the placement and presentation rate (FOV and ROV) of subsequent single or multiple target items.

The general strategy for executing this innovation is as follows. When supra-threshold targets are perceived, represented and responded to (as determined by the rules of the game), the difficulty is escalated by increasing the spatial eccentricity (FOV), decreasing the spatial distances between targets at a given FOV and/or increasing the temporal rate (ROV) at which new targets are presented. If these are not responded to appropriately, the difficulty is reduced toward the initial supra-threshold level. When targets are successfully perceived, represented and responded to, then that level of spatiotemporal complexity is taken as the new starting level, and the difficulty is gradually increased again until player's actual spatial and temporal information perception, representation and processing thresholds are determined.

Rather than adopting a common game development paradigm that divides a game into levels of difficulty and uses informal methods to determine the content, "feel" and difficulty of each level, the system uses an adaptive-programming methodology to implement a factor that distinguishes it from existing games: that of player-dependent stimulation of the spatial and temporal information-processing systems based specifically on the player's current spatial and/or temporal crowding thresholds. In general terms, adaptive game development is common and dates back to the beginning of video games and even typing tutors. Thus, it can be thought of as an aspect of the system that does not need to be developed or proved. Variants of adaptive game design are referred to as "Dynamic Game Balancing" or Game "Artificial Intelligence" (AI). While adaptive AI methods, like genetic algorithms or artificial neural networks can be used, alternate adaptive methods entail using common adaptive functions that are used in psychophysical experimentation, such as the "Parameter Estimation by Sequential Testing (PEST)" technique (see Leek, M. R.: Adaptive procedures in psychophysical research. *Perception & Psychophysics* 63, 1279-1292 (2001)) may also prove just as effective.

All of these techniques are variants of the same general approach. However, at present, all the similar techniques work in a different fashion from the proposed technique. Existing techniques use player performance data in order to decide when changes in game difficulty should be introduced. However, none of these existing techniques are focused on spatiotemporal representational crowding, and none uses the thresholding technique presented here, nor does any have access to the scientific data on which it is based in order to determine when to make changes, by how much, in which direction and in which domain (i.e., spatial or temporal).

In the general technique used by our system, initial parameters are set as described above, and then a log of all user actions is created and continually analyzed to determine patterns that relate solely to whether specific "hit" or "miss" criteria are being met by the player. These are determined by the level of the game being played at the time and the characteristics of the player. The technique generally operates as follows. Initially, the game presents all target stimuli within the central circle (FOV1) and at the initial presentation rate (ROV1), as described above and defined by the research studies (see FIG. 5). What separates our new game from existing games and what could not be achieved by their use is that: (a) only specific components of game play are changed based on continuous dynamic elements of the player's performance (i.e., FOV and ROV); and (b) the initial crowding thresholds and the degree of change are determined by detailed scientific analysis of actual human performance data.

Player actions are categorized as either primary or secondary target-dependent actions. While the specific "cover story" or game goals and art/character choices do not affect the behavior of the game (i.e., all such choices are variants of the identical game), they determine the categorization of specific actions into primary and secondary. An exemplary embodiment is described below, but there is nothing specific to this design that is required. Any story line or character set found to be engaging by game players can be used. In the current example, the aFP-POV game is one in which the player has to control a frog whose goal is to grab passing flies (i.e. targets) to eat by shooting out its tongue. Player actions involved with moving characters (i.e., the frog) or positioning/angling a "weapon" (i.e., its head/tongue) are categorized as secondary actions. Player actions required for actual "firing" (i.e., shooting out the tongue) are categorized as primary actions. Depending on the specific goals of the game and the description of the target items, the immediate game conditions following player primary actions are categorized as either "hits" or "misses." In the present example, a "hit" is generally defined when the user fires a "round" (the frog's tongue") from a "weapon" (a specific frog) in such a way that it makes contact with (grabs and then swallows) a target object (a fly). It is envisioned that at least the 4 following types of events will be used to define hits and misses. A Successful Hit occurs when the player successfully hits a target, as just described. A Miss:Incorrect-Location occurs when the player misses a target on the screen by some design- or algorithm-determined criterion based on scientific evidence or current player ability within a game. For example, this could be as much as 45 degrees or little as 5 degrees or less. A Miss:Incorrect-Timing occurs when the player shoots at the correct location at a target that has recently disappeared. A Miss:Incorrect-Timing-And-Location—occurs when a player shoots but fails to meet any of the above timing or location criteria. Depending on the demands of the game being presented to a specific player (or member of a player category) at a given point in the game being played, there is a threshold for adaptation of the spatial or temporal demands of the task. For example, the player may have reached a stage in game play where it would require failing to hit 10 targets presented (at or below the currently specified threshold in the spatial or temporal domains) with no misses in order for a reduction of difficulty to be introduced. This is an example of game play at a high level of difficulty. Much earlier in game play, the same player may only required to miss one to three items below his/her current spatial or temporal crowding threshold for a reduction in difficulty to be made. One embodiment operates flexibly at the start of play because, even though empirically derived threshold values would have been generated for the individual or group, these would not have been measured within the context of the aFP-POV game. Therefore, in order to keep the player engaged and motivated, early stages of game play can be very flexible in order to keep the hit rate quite high for the player. This encourages continued play and optimizes the therapeutic impact of the game for the player.

Because the location of all objects in the FOV is known to the game program at all times, records can be kept of which of the three types of misses described above have occurred. If the player exceeds the current hit rate criterion, then the game adjusts the difficulty of presented target items according to the ongoing log of the player's performance. If the current hit rate criterion is achieved but greater progress was made in spatial than temporal terms (i.e., fewer spatial and more temporal errors were made), then objects are presented at the next most difficult spatial eccentricity (i.e., FOV2 following initial play or the next concentric circle out, FOVn+1). If the hit rate criterion is achieved but more progress was made in temporal terms (i.e., fewer temporal and more spatial errors were made), then objects start to be presented at the next most difficult rate of viewing (i.e., ROV2 following initial play, or the next smallest delay time between presentation of one target item and the next, ROVn+1). Similarly, if the player meets the miss rate criterion, then spatial and/or temporal difficulty is adjusted in the same fashion, by presenting target stimuli at FOVn−1 and/or ROVn−1. Feedback given to secondary, and any other behaviors, is purely cosmetic (as in providing auditory or visual "rewards"), but the behavior of the game is unaffected. The focus of game adaptation in response only to primary spatiotemporal actions, which can only be generated for stimuli above the player's current crowding thresholds, is another unique aspect of our game. If this is changed, then the game would be unlikely to achieve its goals, and would be much less easily distinguished from other aFP-POV games that currently exist but are not targeted at engendering change in spatiotemporal information-processing systems.

In order to reduce spatial and temporal crowding by increasing resolution as well as simply increasing the spread and speed of attention, as can effected with single targets, it is necessary to have the functionality of manipulating spatial and temporal distances between targets. To increase the spatial resolution of visual attention requires each FOV to be subdivided into a maximum of 120 subcomponents of 1 arcmin each, as described above. Resolution for attentional processing of visually presented information at least is both coarser than that for simple vision and it becomes steeply more coarse, by a factor of at least 20 by 15 degrees of eccentricity in healthy adult human observers, as view point moves from the center (see Intriligator, J. & Cavanagh, P. The spatial resolution of visual attention. *Cognitive psychology* 43, 171-216 (2001). Thus, to increase spatial resolution, two targets are presented initially within the central ring where resolution is highest. The targets are placed at its center and on the FOV=2 circle, i.e. at 2 degrees of visual angle separation. The standard performance criteria apply and the algorithm would be expected, at this level, to increase difficulty, for example by reducing the spacing by half the distance (here 60 arcmin or 1 degree) when the operational performance threshold (e.g. 80% correct) is determined. The game can operate using single spatial targets (i.e. to focus solely on temporal resolution). In this case all spatial distances are calculated in terms of 2 degree eccentricities with reference to the center of the display, or origin. In the more common dual spatial target case (to enhance both spatial and temporal resolution) spatial distances are calculated between one target and the other, where the initial pair always has one target placed at the origin. If the resulting distance of the first adjustment is too small and induces spatial crowding, then, as always, the distance between the two targets is increased, e.g. by 50%, which, in this case is 30 arcmin. Once the player has reached a stable performance threshold (e.g. a success rate of 80% at an inter-target distance below 2 degrees) and cannot do so at a smaller distance, a process very like that used for single targets is used. Specifically, new pairs of targets will begin to appear in the next most concentric ring, still employing the normal distribution algorithm to bias attention to the central location. Initially, targets will be spaced 2 degrees apart (i.e. appearing on each of the two boundary circles) and distance between them will be adjusted as described above. Since the resolution of spatial attention degrades significantly with increasing eccentricity, it is expected that the final inter-target distance required to successfully represent and identify (and thus hit) targets, i.e. above the crowding threshold, will be larger than in rings closer to the center. However, for the special populations that are targets for the present intervention, those values are not currently known.

Finally, as with any typical game, our game can be organized into several levels, where each new level becomes "unlocked" after a certain degree of success at the lower levels. This feature is used to maintain interest and engage the player for a longer period of time than if the same environment and artistic characteristics were used throughout. Each new level can be slightly more difficult than the one before (i.e., the new level starts at the highest FOV/ROV levels achieved in the previous level) and can provide new game assets or characters in order to maintain interest. For example, new levels may offer new animals, such as lizards that catch different flies or fish that catch small marine creatures (or bubbles) and different backgrounds, music and other cosmetic artistic changes to complement the new thematic elements. At the highest levels, the player may even be able to gain more than one aFP-POV character to control at the same time, such as the case where two frogs might be trying to catch flies at the same time and the player must divide their cognitive resources between them in order to make sure that one does not miss out and leave the playing area to go find food somewhere else.

System

FIG. 1 illustrates a viewing angle for a user 102 interacting with a video game that executes on a computer system 106 in accordance with the disclosed embodiments. During operation of the video game, a user 102 views the video game through a display 104 that is attached to computer system 106, and also inputs commands into the video game through a controller 105, which is attached to computer system 106. In general, controller 105 can include any type of input device that can be used to input commands into a video game, including a game controller with a joystick, a keyboard, or a pointing device such as a mouse.

Note that display 104 is located a specific distance 103 from user 102, which causes display 104 to occupy a range of viewing angles 107. The display geometries of the video game are scaled so that objects, which are presented to user 102 through display 104, have a specific viewing angle relative to the center of the display.

Game Operation

Figure 2:
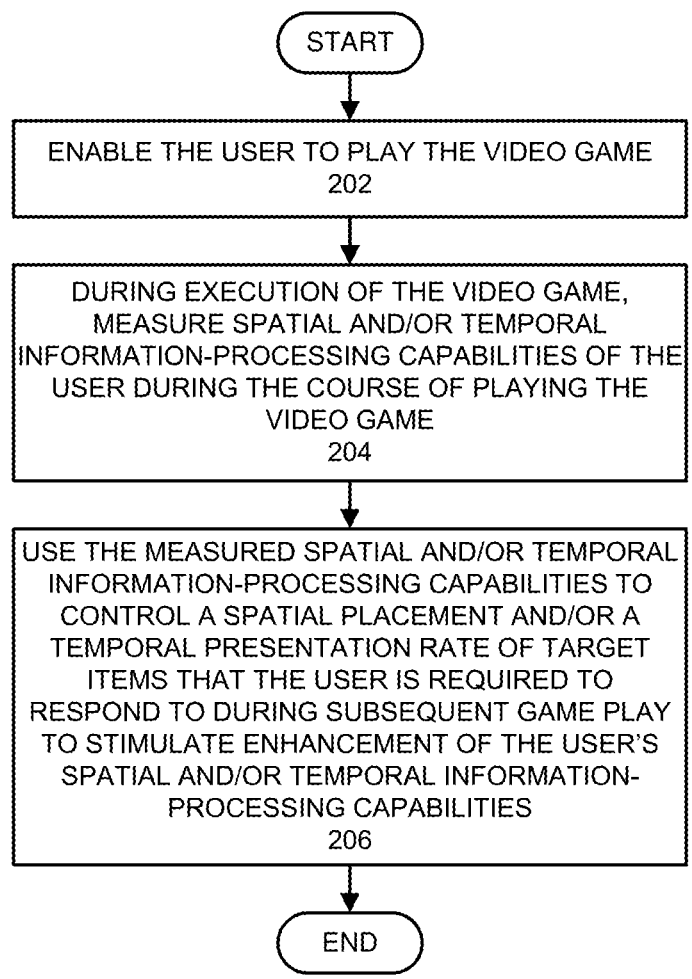
FIG. 2 presents a flow chart illustrating how the video game operates in accordance with the disclosed embodiments.

FIG. 2 presents a flow chart illustrating how the system operates in accordance with the disclosed embodiments. During operation, the system enables the user to play the video game (step 202). Note that this may involve first performing a calibration step to calibrate a visual angle between target items that are presented on a display for the video game. For example, this calibration step may involve determining the size of the display and how far away the user is from the display, and then spatially scaling the presentation of the video game in the display so that distances associated with target items in the display have specific visual angles.

While enabling the user to play the video game, the system first measures spatial and/or temporal information-processing capabilities in terms of crowding thresholds of the user during the course of playing the video game (step 204). Next, the system uses the measured spatial and/or temporal information-processing capabilities to control a spatial placement and/or a temporal presentation rate of target items that the user is required to respond to during subsequent game play to stimulate enhancement of the user's spatial and/or temporal information-processing capabilities (step 206).

Figure 3:
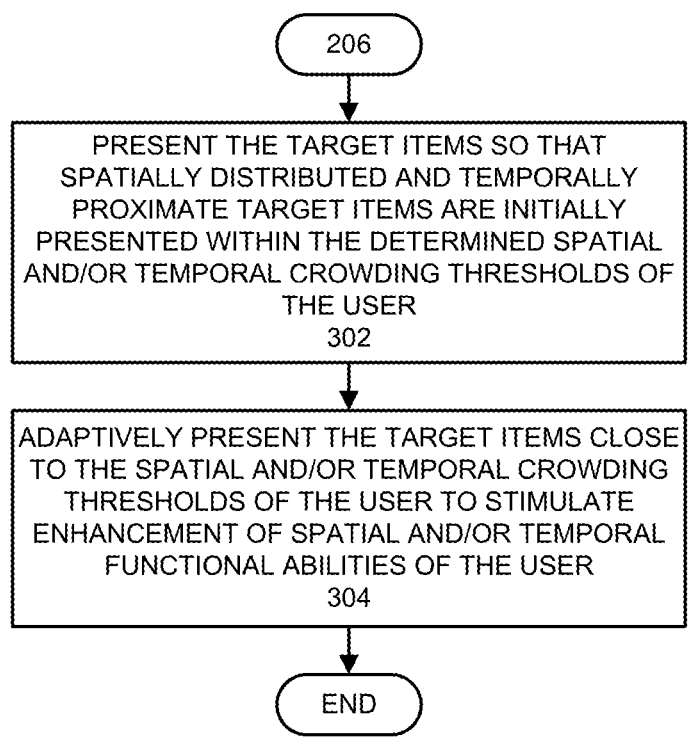
FIG. 3 presents a flow chart that provides additional details about how the video game operates in accordance with the disclosed embodiments.

FIG. 3 presents a flow chart that provides additional details about how the video game operates during step 206 in the flow chart in FIG. 2 in accordance with the disclosed embodiments. The system first presents the target items so that spatially distributed and temporally proximate target items are initially presented within the determined spatial and/or temporal crowding thresholds of the user (step 302). Next, the system adaptively presents the target items close to the spatial and/or temporal crowding thresholds of the user to stimulate enhancement of spatial and/or temporal functional abilities of the user (step 304).

Figure 4:
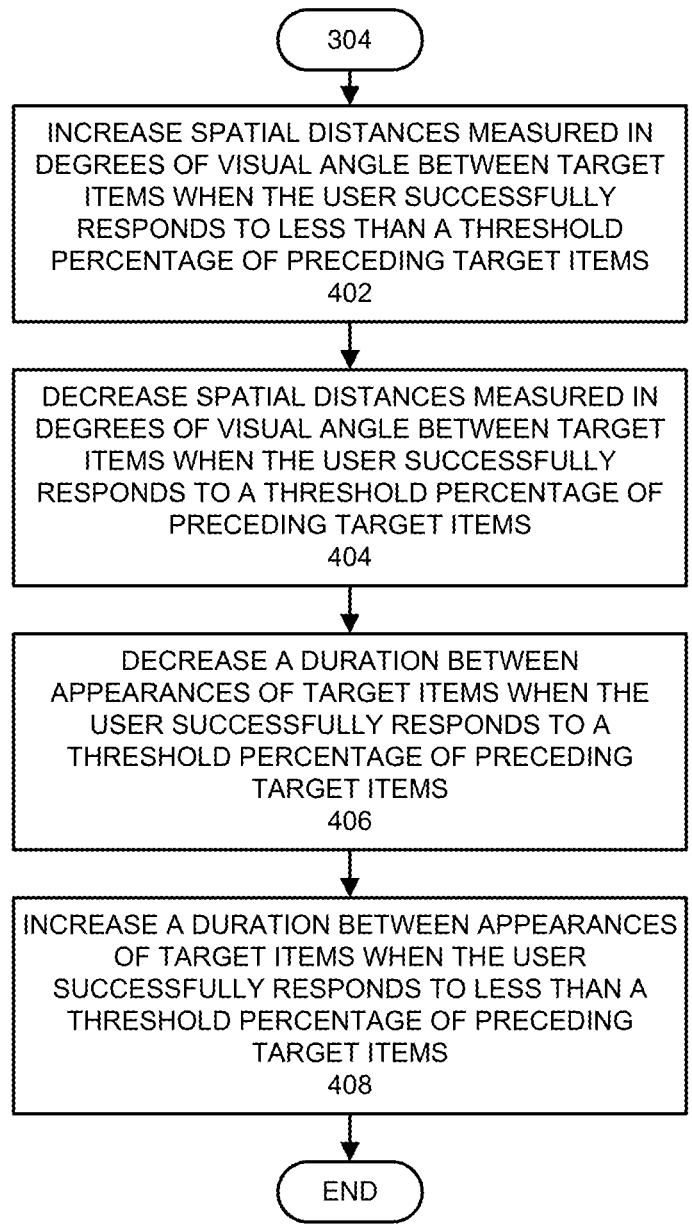
FIG. 4 presents a flow chart illustrating how visual angles and durations between appearances of target items are adjusted in accordance with the disclosed embodiments.

FIG. 4 presents a flow chart illustrating how distances, measured in terms of complete of divisions of visual angles and durations between appearances of target items are adjusted in step 304 of the flow chart that appears in FIG. 3 accordance with the disclosed embodiments. During operation, the system dynamically performs a number of adjustments. The system increases spatial distances measured in degrees of visual angle between target items when the user successfully responds to less than a threshold percentage of preceding target items (step 402). The system decreases spatial distances measured in degrees of visual angle between target items when the user successfully responds to a threshold percentage of preceding target items (step 404). The system decreases a duration between appearances of target items when the user successfully responds to a threshold percentage of preceding target items (step 406). Finally, the system increases a duration between appearances of target items when the user successfully responds to less than a threshold percentage of preceding target items (step 408).

Field of View

FIG. 5 presents an exemplary field of view 500 for a video game in accordance with the disclosed embodiments. The center of field of view 500 comprises a focal point 502 surrounded by a set of concentric circles (FOV1, FOV2, FOV3, FOV4, FOV5, FOV6, FOV7, and FOV8), which have different visual angles relative to focal point 502. More specifically, FOV1 is located two degrees of visual angle away from focal point 502, and each successive concentric ring is located two degrees farther away from focal point 502. During operation of the video game using single spatial targets, target items appear at the intersections between the eight radial lines illustrated in FIG. 5 and the set of concentric circles (FOV1, FOV2, FOV3, FOV4, FOV5, FOV6, FOV7, and FOV8). During operation of the game using dual spatial targets, one target item appears at this point on each of two contiguous circles or, initially, one at the origin and the other at this point at ring FOV1] When a player sees a target item, the player moves an input device, such as a joystick, in a direction that is consistent with the associated radial line to indicate that the player has detected, mentally represented and identified the object as a target item. Note that the default starting state for this embodiment includes 8 radial lines associated with eight possible directions for the input device. However, the system can stimulate resolution by having the capacity to increase this from 8 to 16, to 32 to 64 or even more radial lines to require ever more fine-grained detections and motor responses to be made.

Empirical Performance Measurements

A single target implementation of the above-described video game was tested on a number of subjects. The default playing time for the video game was set to five minutes, wherein game play can be extended by successful "streaks"

of 7+ hits in a row. The maximum FOV/ROV values were set to 10, and the version of the game represented here adjusted values quickly in windows of just 10 targets (e.g. 7/10=70%, which induced a change in ROV/FOV). Note that other versions of the video game adapt much more slowly to allow for longer playing time.

Figure 6A:
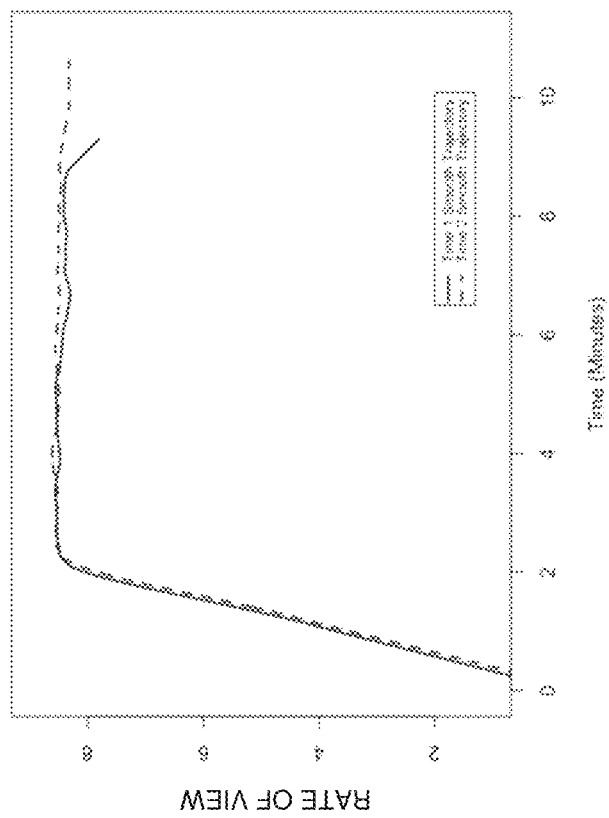
FIGS. 6A-6B present graphs illustrating the performance of an expert gamer while playing the video game in accordance with the disclosed embodiments.
Figure 6B:
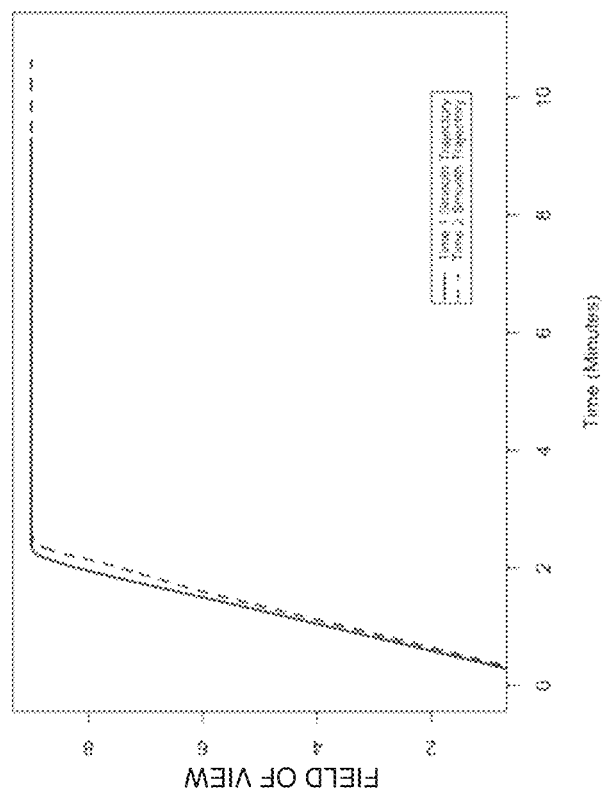

FIGS. 6A-6B present graphs illustrating the performance of a young, male expert gamer while playing the video game in accordance with the disclosed embodiments. In particular, FIG. 6A illustrates field of view and FIG. 6B represents rate of view. Note that while the expert gamer is playing, the system adapts rapidly to a high level in both the FOV and ROV graphs and the performance of the expert gamer remains at these high levels throughout the duration of the game.

Figure 7A:
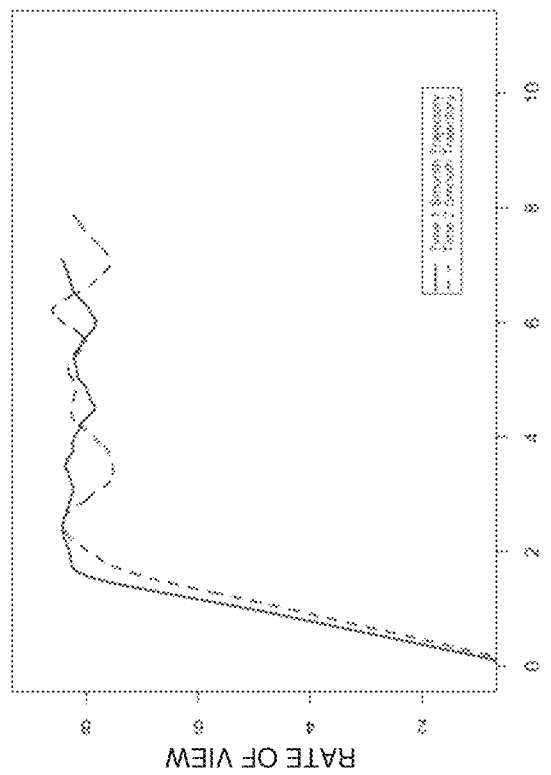
FIGS. 7A-7B present graphs illustrating the performance of a moderate-level player while playing the video game in accordance with the disclosed embodiments.
Figure 7B:
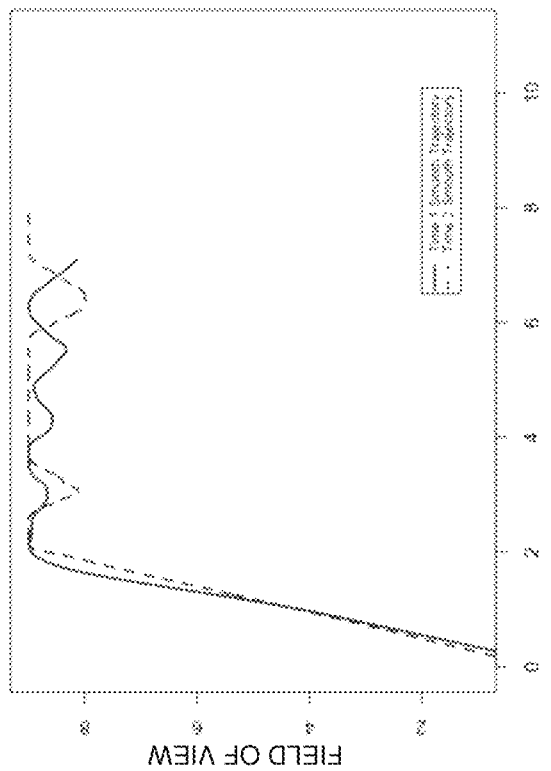

FIGS. 7A-7B present graphs illustrating the performance of a similarly aged female moderate-level gamer while playing the video game in accordance with the disclosed embodiments. While this moderate-level gamer is playing the game, the system also adapts rapidly to a high level in both the FOV and ROV graphs. However, the ongoing performance of this moderate-level gamer is somewhat less consistent than the performance of the expert gamer as can be seen from the graphs in FIGS. 7A-7B.

Figure 8A:
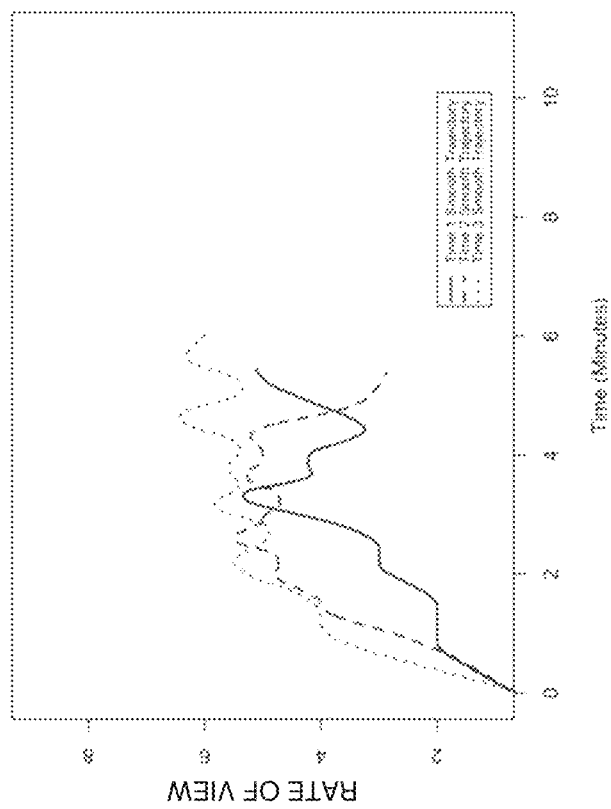
FIGS. 8A-8B present graphs illustrating the performance of a young player with a neurodevelopmental disorder while playing the video game in accordance with the disclosed embodiments.
Figure 8B:
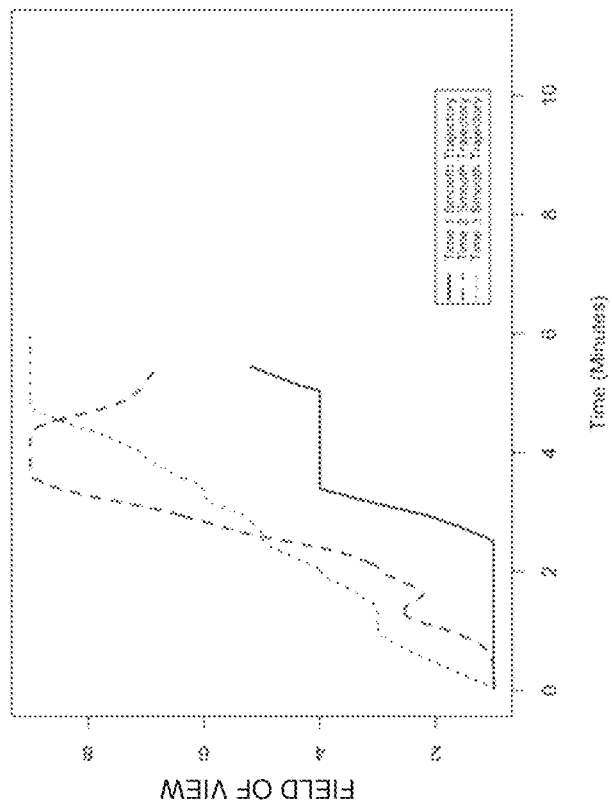

FIGS. 8A-8B present graphs illustrating the performance of a seven-year-old player with a neurodevelopmental disorder while playing the video game in accordance with the disclosed embodiments. Note that the first time this player played the game, he made very slow progress in both FOV and ROV measures. The FOV performance improved greatly the second and third times the player played the game. The ROV also improved the second and third times, but not as much as the FOV improved.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for using a video game to improve spatial and temporal information-processing capabilities of a user, wherein the video game operates by:
    displaying on a display device at least two target items in a current field of view, wherein the current field of view comprises one of multiple logical concentric circles defined upon but not displayed on the display device;
    controlling spatial placement and a temporal presentation rate of the target items in the field of view;
    receiving the user's response to the display of the target items, said response comprising an attempt to hit at least one of the at least two target items with a single motion;
    determining a hit rate, a miss rate or a combination of hit rate and miss rate based on the user's response;
    comparing the hit rate, the miss rate or a combination of the hit rate and the miss rate to a current rate criterion;
    adjusting difficulty based on the comparison, wherein the difficulty comprises the spatial placement and the temporal presentation rate for subsequent target items; and
    displaying on the display device the subsequent target items at the adjusted difficulty.

2. The method of claim 1, wherein if the hit rate exceeds the current rate criterion, the subsequent target items are presented at a higher difficulty, wherein the difficulty is escalated by decreasing the spatial distances between targets in the current field of view, increasing the field of view, increasing the temporal presentation rate at which new targets are presented or a combination thereof.

3. The method of claim 2, wherein the hit rate comprises a temporal hit rate and the current rate criterion comprises a current temporal hit rate criterion, and wherein the difficulty is escalated by increasing the temporal presentation rate at which new targets are presented when the comparison indicates that the temporal hit rate exceeds the temporal hit rate criterion.

4. The method of claim 3, wherein the difficulty is reduced by increasing the spatial distances between targets at the current field of view when the comparison indicates that the spatial miss rate exceeds the current spatial miss rate criterion.

5. The method of claim 3, wherein the difficulty is reduced by decreasing the field of view when the comparison indicates that the spatial miss rate exceeds the current spatial miss rate criterion.

6. The method of claim 3, wherein the miss rate comprises a temporal miss rate and the current miss rate criterion comprises a current temporal miss rate criterion, and wherein the difficulty is reduced by decreasing the temporal presentation rate at which new targets are presented when the comparison indicates that the temporal miss rate exceeds the temporal miss rate criterion.

7. The method of claim 1, wherein the hit rate comprises a spatial hit rate and the current rate criterion comprises a current spatial hit rate criterion.

8. The method of claim 7, wherein the difficulty is escalated by decreasing the spatial distances between targets in the current field of view when the comparison indicates that the spatial hit rate exceeds the current spatial hit rate criterion.

9. The method of claim 7, wherein the difficulty is escalated by increasing the field of view when the comparison indicates that the spatial hit rate exceeds the spatial hit rate criterion.

10. The method of claim 1, wherein if the miss rate exceeds a current miss rate criterion, the subsequent target items are presented at a reduced difficulty, wherein the difficulty is reduced by increasing the spatial distances between targets at the current field of view, decreasing the field of view, decreasing the temporal presentation rate at which new targets are presented or a combination thereof.

11. The method of claim 1, wherein the miss rate comprises a spatial miss rate and the current miss rate criterion comprises a current spatial miss rate criterion.

12. The method of claim 1, wherein the spatial placement for subsequent target items comprises adjusting the degree of visual angle between two or more target items.

13. The method of claim 1, further comprising initially presenting the target items above a crowding threshold of the user.

14. The method of claim 13, wherein the crowding threshold is a spatial crowding threshold, a temporal crowding threshold or both a spatial crowding threshold and a temporal crowding threshold.

15. The method of claim 1, wherein at least one of the target items is presented in a central area of the field of view.

16. A non-transitory computer-readable storage medium storing instructions that when executed by a computer cause the computer to perform a method for using a video game to improve spatial and/or temporal information-processing capabilities of a user, the method comprising:
displaying on a display device at least two target items in a current field of view, wherein the current field of view comprises one of multiple logical concentric circles defined upon but not displayed on the display device;
controlling spatial placement and a temporal presentation rate of the target items in the field of view;
receiving the user's response to the display of the target items, said response comprising an attempt to hit at least one of the at least two target items with a single motion;
determining a hit rate, a miss rate or a combination of hit rate and miss rate based on the user's response;
comparing the hit rate, the miss rate or a combination of the hit rate and the miss rate to a current rate criterion;
adjusting difficulty based on the comparison, wherein the difficulty comprises the spatial placement and the temporal presentation rate for subsequent target items; and
displaying on the display device the subsequent target items at the adjusted difficulty.

17. The non-transitory computer-readable storage medium of claim 16, wherein if the hit rate exceeds the current rate criterion, the subsequent target items are presented at a higher difficulty, wherein the difficulty is escalated by decreasing the spatial distances between targets in the current field of view, increasing the field of view, increasing the temporal presentation rate at which new targets are presented or a combination thereof.

18. The non-transitory computer-readable storage medium of claim 16, wherein the hit rate comprises a spatial hit rate and the current rate criterion comprises a current spatial hit rate criterion, and wherein the difficulty is escalated by decreasing the spatial distances between targets in the current field of view or by increasing the field of view when the comparison indicates that the spatial hit rate exceeds the current spatial hit rate criterion.

19. The non-transitory computer-readable storage medium of claim 16, wherein the hit rate comprises a temporal hit rate and the current rate criterion comprises a current temporal hit rate criterion, and wherein the difficulty is escalated by increasing the temporal presentation rate at which new targets are presented when the comparison indicates that the temporal hit rate exceeds the temporal hit rate criterion.

20. The non-transitory computer-readable storage medium of claim 16, wherein if the miss rate exceeds a current miss rate criterion, the subsequent target items are presented at a reduced difficulty, wherein the difficulty is reduced by increasing the spatial distances between targets at the current field of view, decreasing the field of view, decreasing the temporal presentation rate at which new targets are presented or a combination thereof.

21. The non-transitory computer-readable storage medium of claim 16, wherein the miss rate comprises a spatial miss rate and the current miss rate criterion comprises a current spatial miss rate criterion, and wherein the difficulty is reduced by increasing the spatial distances between targets at the current field of view or by decreasing the field of view when the comparison indicates that the spatial miss rate exceeds the current spatial miss rate criterion.

22. The non-transitory computer-readable storage medium of claim 16, wherein the miss rate comprises a temporal miss rate and the current miss rate criterion comprises a current temporal miss rate criterion, and wherein the difficulty is reduced by decreasing the temporal presentation rate at which new targets are presented when the comparison indicates that the temporal miss rate exceeds the temporal miss rate criterion.

23. The non-transitory computer-readable storage medium of claim 16, wherein the difficulty comprises both the spatial placement and the temporal presentation rate for subsequent target items.

24. The non-transitory computer-readable storage medium of claim 16, further comprising initially presenting the target items above a crowding threshold of the user, wherein the crowding threshold is a spatial crowding threshold, a temporal crowding threshold or both a spatial crowding threshold and a temporal crowding threshold.

25. A system that operates a video game to improve spatial and/or temporal information-processing capabilities of a user, the system comprising:
at least one processor and at least one associated memory; and
a computer program that executes on the at least one processor, wherein during operation the computer program:
displays on a display device at least two target items in a current field of view, wherein the current field of view comprises one of multiple logical concentric circles defined upon but not displayed on the display device;
controls spatial placement and a temporal presentation rate of the target items in the field of view;
receives the user's response to the display of the target items, said response comprising an attempt to hit at least one of the at least two target items;
determines a hit rate, a miss rate or a combination of hit rate and miss rate based on the user's response;
compares the hit rate, the miss rate or a combination of the hit rate and the miss rate to a current rate criterion;
adjusts difficulty based on the comparison, wherein the difficulty comprises the spatial placement, the temporal presentation rate or a combination thereof for subsequent target items; and
displays on the display device the subsequent target items at the adjusted difficulty.

26. The system of claim 25, wherein the display device offers the user a three-dimensional display of the field of view.

* * * * *